(12) United States Patent
Vitt et al.

(10) Patent No.: US 6,727,100 B1
(45) Date of Patent: Apr. 27, 2004

(54) METHOD OF IDENTIFYING CANDIDATE MOLECULES

(75) Inventors: Daniel Vitt, Planegg-Martinsried (DE); Stefan Busemann, Munich (DE); Ulrich Dauer, Isen (DE)

(73) Assignee: 4SC AG, Planegg-Martinsried (DE)

( * ) Notice: Subject to any disclaimer, the term of this patent is extended or adjusted under 35 U.S.C. 154(b) by 29 days.

(21) Appl. No.: 09/693,731

(22) Filed: Oct. 20, 2000

Related U.S. Application Data (63) Continuation-in-part of application No. 09/422,303, filed on Oct. 21, 1999, now abandoned.

(30) Foreign Application Priority Data

Feb. 29, 2000 (DE) .......................................... 100 09 479

(51) Int. Cl.$^7$ ................................................ G06F 19/00
(52) U.S. Cl. .......................................... 436/164; 702/19
(58) Field of Search .............................. 436/164; 702/19

(56) References Cited

U.S. PATENT DOCUMENTS

| | | | |
|---|---|---|---|
| 5,555,366 A | 9/1996 | Teig et al. .................. | 395/161 |
| 5,583,973 A | 12/1996 | DeLisi et al. ................ | 395/120 |
| 5,784,294 A | * 7/1998 | Platt et al. .................... | 702/27 |
| 5,811,231 A | * 9/1998 | Farr et al. ...................... | 435/6 |
| 6,389,378 B2 | 5/2002 | Itai et al. ...................... | 703/11 |

* cited by examiner

Primary Examiner—Jill Warden
Assistant Examiner—Monique T. Cole
(74) Attorney, Agent, or Firm—Davidson, Davidson & Kappel, LLC (57) ABSTRACT

A method of identifying candidate molecules expected to be biologically active comprises the following steps: Creating a set consisting of different molecules; to each of said molecules of said set, assigning a descriptor representing a predetermined number of molecular properties; mapping said set of molecules onto points of a two-dimensional grid with regard to a predetermined similarity relation of the respective assigned descriptors such that the grid distance between grid points of two molecules is a measure for the similarity of said two molecule descriptors; forming a three-dimensional surface over said grid of molecules, said surface representing the distribution of biological activity of the molecules on the grid approximatively according to a predetermined quality criterion; selecting from said three-dimensional surface candidate molecules satisfying a predetermined criterion with respect to their biological activity.

27 Claims, 14 Drawing Sheets

```
 6

269.80    2  5  4  1  3   BTB_03049
229.80    6  5  1  2  4   SPB_00387
259.85    4  3  2  1  1   EN_00236
179.05    4  2  0  0  2   NRB_00265
```

```
6
269.80  2  5  4  1  3  BTB_03049
229.80  6  5  1  2  4  SPB_00387
259.85  4  3  2  1  1  EN_00236
179.05  4  2  0  0  2  NRB_00265
```

Fig. 7 shows an a sorted data set on the map for an example of a data set of 40000 molecules

Thrombin

| Iterations | Hits | Max Hits | % |
|---|---|---|---|
| 0 | 0 | 1894 | 0,00% |
| 97 | 26 | 1894 | 1,37% |
| 192 | 100 | 1894 | 5,28% |
| 279 | 149 | 1894 | 7,87% |
| 367 | 161 | 1894 | 8,50% |
| 455 | 197 | 1894 | 10,40% |
| 543 | 218 | 1894 | 11,51% |
| 626 | 275 | 1894 | 14,52% |
| 706 | 314 | 1894 | 16,58% |
| 797 | 408 | 1894 | 21,54% |
| 879 | 478 | 1894 | 25,24% |
| 968 | 540 | 1894 | 28,51% |
| 1052 | 608 | 1894 | 32,10% |
| 1129 | 637 | 1894 | 33,63% |
| 1212 | 777 | 1894 | 41,02% |
| 1290 | 831 | 1894 | 43,88% |
| 1366 | 940 | 1894 | 49,63% |
| 1442 | 968 | 1894 | 51,11% |
| 1522 | 1043 | 1894 | 55,07% |
| 1591 | 1087 | 1894 | 57,39% |
| 1667 | 1192 | 1894 | 62,94% |
| 1741 | 1335 | 1894 | 70,49% |
| 1817 | 1598 | 1894 | 84,37% |
| 1889 | 1623 | 1894 | 85,69% |
| 1960 | 1701 | 1894 | 89,81% |
| 2057 | 1739 | 1894 | 91,82% |

Fig. 10

DHFR

| Iterations | Hits | Max Hits | % |
|---|---|---|---|
| 0 | 0 | 1198 | 0,00% |
| 97 | 11 | 1198 | 0,92% |
| 194 | 42 | 1198 | 3,51% |
| 285 | 51 | 1198 | 4,26% |
| 367 | 83 | 1198 | 6,93% |
| 458 | 106 | 1198 | 8,85% |
| 546 | 159 | 1198 | 13,27% |
| 638 | 167 | 1198 | 13,94% |
| 723 | 176 | 1198 | 14,69% |
| 807 | 209 | 1198 | 17,45% |
| 895 | 216 | 1198 | 18,03% |
| 974 | 247 | 1198 | 20,62% |
| 1059 | 294 | 1198 | 24,54% |
| 1138 | 312 | 1198 | 26,04% |
| 1220 | 332 | 1198 | 27,71% |
| 1296 | 343 | 1198 | 28,63% |
| 1368 | 350 | 1198 | 29,22% |
| 1439 | 379 | 1198 | 31,64% |
| 1512 | 385 | 1198 | 32,14% |
| 1589 | 466 | 1198 | 38,90% |
| 1666 | 491 | 1198 | 40,98% |
| 1765 | 499 | 1198 | 41,65% |
| 1865 | 547 | 1198 | 45,66% |
| 1965 | 717 | 1198 | 59,85% |
| 2065 | 746 | 1198 | 62,27% |

Fig. 11

METHOD OF IDENTIFYING CANDIDATE MOLECULES

RELATED APPLICATIONS

The present application is a continuation-in-part of U.S. Ser. No. 09/422,303 filed Oct. 21, 1999, now abandoned.

The present invention relates to a method of identifying candidate molecules expected to be biologically active.

Evaluating receptor or target suitability of molecules is an important task in pharmaceutical drug research. With the increasing employment of automation techniques over the last years within Drug Discovery processes, methods like High-Throughput-Screening (HTS) and High-Throughput-Synthesis have become industry standards in pharmaceutical research. Nowadays, it is possible to test more than 20,000 molecules per day for their biological activities in certain disease targets. Also in the area of chemical synthesis, combinatorial chemistry in combination with automation processes, hundreds of molecules per day can be made physically available. Since based on today's chemical knowledge, more than $10^{100}$ molecules could theoretically be synthesized and tested and several hundreds of thousands molecules are commercially available, computer assisted methods have been developed to select subsets of molecules which are actually supposed to be tested based on their predicted potential of biological activity for certain disease targets.

Two categories of computer assisted methods serve the purpose of discovering (selecting and/or prioritizing) molecules from data sets of theoretically available molecules for biological activity testing. The first category comprises diversity or similarity based discovery methods, whereas the second category comprises structure based discovery methods. Among the second category, there are database search techniques, as well as (Q)SAR methods and Docking methods.

Only the (Q)SAR methods and the Docking methods implicitly consider information related to specific targets, either common structural patterns of a series of active molecules ((Q)SAR) or the 3-dimensional structure of a target protein (Docking) and therefore deliver the most specific results. In practice, methods based on (Q)SAR or Docking are applied to smaller data sets (up to 50,000 sets), since they need relatively high computing power. However, although parallel computing techniques can be used to gain speed, still data sets consisting of more than $10^6$ molecules are not predictable with respect to their biological activity in a reasonable time frame.

The term biological activity is hereinafter used to comprise in particular pharmaceutical as well as agrochemical activity with respect to a certain receptor or target.

The search for candidate molecules also comprises the search for lead compounds.

SUMMARY OF THE INVENTION

It is therefore an object of the present invention to provide a method of and a system for finding candidate molecules expected to be biologically active, which method and system can be applied on molecule libraries comprising high amounts of data and yields results in a reasonable time.

According to the invention, the method of identifying candidate molecules expected to be biologically active, comprises the following steps:
a) creating a set consisting of different molecules;
b) to each of said molecules of said set, assigning a descriptor representing a predetermined number of molecular properties;
c) mapping said set of molecules onto points of a two-dimensional grid with regard to a predetermined similarity relation of the respective assigned descriptors such that the grid distance between grid points of two molecules is a measure for the similarity of said two molecule descriptors;
d) forming a three-dimensional surface over said grid of molecules, said surface representing the distribution of biological activity of the molecules on the grid approximatively according to a predetermined quality criterion;
e) selecting from said three-dimensional surface candidate molecules satisfying a predetermined criterion with respect to their biological activity.

According to the invention, said three-dimensional surface in step d) may be formed by applying the following steps:
da) taking the whole two-dimensional grid as initial region of approximation;
db) selecting molecules on predetermined grid points of said region, and calculating their respective values of biological activity;
dc) approximating the surface over said region using said previously determined values of biological activity of said molecules on said predetermined grid points;
dd) determining whether said approximated surface satisfies a predetermined quality criterion; if so, goto step e); if not so, refining the approximation of the surface by selecting molecules on further grid points, calculating their respective values of biological activity, and repeating step dc) and this step dd).

The method used for forming said three-dimensional surface in step d) is preferably an approximation method of the Delauney Triangulation type.

Thus, the inventive method consists in performing two major steps. In the first step, the molecules are sorted and mapped onto a 2-D grid according to their similarity of their descriptors. In the second step, the biological activity of the mapped molecules is approximated by modelling the distribution as surface over the molecule map. From the surface, suitable candidate molecules for further evaluation can be determined. According to the invention, only a very small amount of molecules within the data set have to be really calculated. This results in a considerable gain of performance. The recursive proceeding allows to study the data base based on customizable quality criteria. Error and quality criteria for the analysis can be tailored according to a given problem. Docking simulations of collections of molecules can easily be run parallel, which additionally leads to a performance gain.

Thus, the method according to the present invention translates predicted/measured biological activity into topographical information of a three-dimensional surface, which is analyzed iteratively, using approximation algorithms. Only those regions of the surface are thoroughly analyzed, that represent regions of high biological activity while those of low binding energies for a given protein binding site are approximated by few data points. Thus, as examples have shown, active molecules can be identified from data sets by explicitly calculating/measuring just 4–6% of the molecules within the data set.

By using the method according to the invention, drug lead candidates can be identified without the need of making large molecule sets physically available and testing them.

The selected candidate molecules are suitable for chemical synthesis.

Preferably, the molecular properties represented by said descriptors are at least two of:
- molecular weight,
- number of rotatable bonds,
- number of hydrophobic groups,
- number of hydrophilic groups,
- number of acid groups,
- number of basic groups,
- number of neutral groups,
- number of zwitter groups,
- number of heavy atoms,
- number of H-bond donors,
- number of H-bond acceptors,
- number of 1–2 dipoles,
- number of 1–3 dipoles,
- number of 1–4 dipoles.

Preferably, said molecule-mapping is performed using self-organizing maps within a neural network or statistical methods like linear vector quantization.

BRIEF DESCRIPTION OF THE DRAWINGS

The invention comprises also a computer system having means for performing the identifying method, means for inputting commands to the system, and means for outputting the result of performing the method.

The invention and examples thereof are described in detail with reference to the accompanying figures, in which FIG. 5 illustrates four intermediate steps of approximation of a surface by Delauney triangulation.

FIG. 6 illustrates the final approximation of the surface by Delauney triangulation.

DETAILED DESCRIPTION

The inventive method is illustrated using the example of finding inhibitors of Dihydrofolatreductase (PDB Code: 4 dfr).

According to the invention, prior to evaluation of particular molecules, the so-called virtual library is created, which comprises all possible molecules. That means that the virtual molecule library contains such molecules which can be purchased or produced with reasonable costs, that are commercially available molecules or molecules which can be produced using combinatorial synthesis approaches. Not comprised are molecules which are a priori not suitable for drug synthesis, in particular such molecules which contain toxic groups, or which have a molecular weight greater then 500 u or more than 5 donors, or molecules having a log P value of greater than 5. The library is held in a computer database.

The database in this example comprises 2,000 molecules. Each of the molecules is represented by 2-D structural data in a machine-readable form.

Upon storing the molecules in the library, a descriptor is assigned to each molecule within the library, which descriptor correlates with the biological activity of the respective molecule. The descriptor is a vector of several scalar molecular properties. This vector comprises the following values:
- molecular weight,
- number of rotatable bonds,
- number of hydrophobic groups,
- number of heavy atoms,
- number of H-bond donors,
- number of H-bond acceptors.

In order to perform a pre-selection of molecules, it is possible to use values covering economical or technical aspects, such as availability and production costs of molecules.

Figure 1:
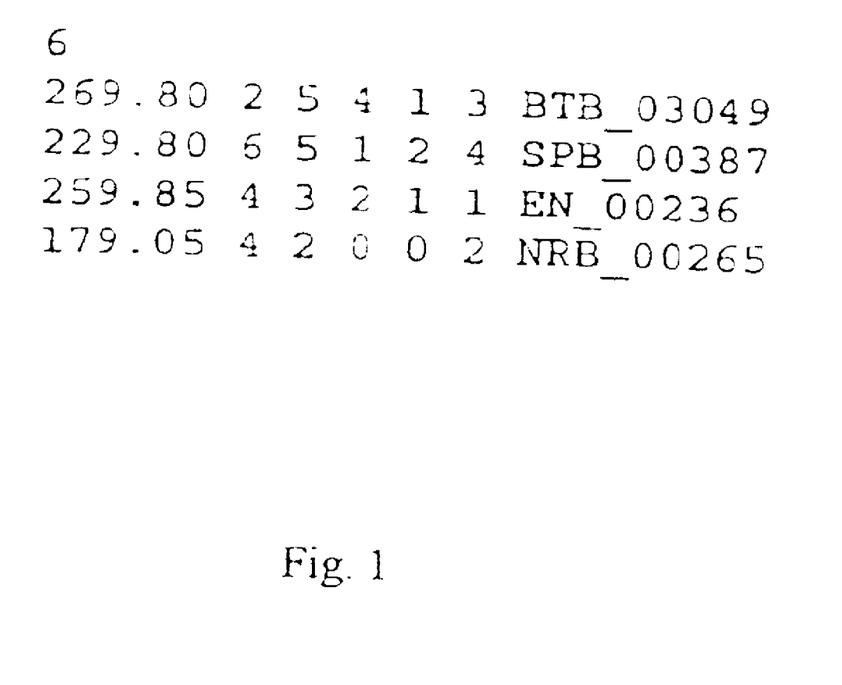
FIG. 1 illustrates the type of descriptor used herein.

FIG. 1 displays four data streams (denoting four molecules) of the descriptor used herein. The first lines specifies the dimension of the descriptor, the second to fifth lines specify the molecules, the last column contains the ID of the corresponding molecules.

The descriptors are adapted for further processing the molecule library in order to find out the molecule candidates for drug synthesis. In order to allow further processing, the descriptors chosen for the molecules of the database are all of the same dimension.

In the next step, the molecules of that library are sorted according to their similarity with regard to potential ligand-receptor-activity. The sorting is performed by mapping the molecules onto a 2-dimensional grid, whereby the similarity of the molecules to each other are represented by the distances of their positions on the grid. The similarity is determined by evaluating the descriptors of the molecules. The sorting is based on a neural network of the Kohonen Self Organizing Map type. Self organizing maps are well-suited since they have been found out to be able to project higher dimensional problems to lower dimension even if there are linear dependencies in the data.

Thus, the sorting is performed in the following way: Initially, all the molecules are put in an arbitrary way onto the grid. The grid must be large enough to comprise all the molecules of the data base. During the learning phases of the neural network, the molecules are propagated over the grid with the aim to bring them into an order with respect to their similarity. Three learning phases are applied. In the first learning phase, the amount of propagation is limited to a grid radius of about 1/10 of the maximum number of grid points in one direction, whereby the convergence is 0.3. In the second learning phase, the radius is one grid point, and the convergence is 0.2; in the third learning phase the radius is 0.5, and the convergence is 0.2. It is to be understood that the grid radius and the convergence may be adapted to the concrete problem.

Figure 2:
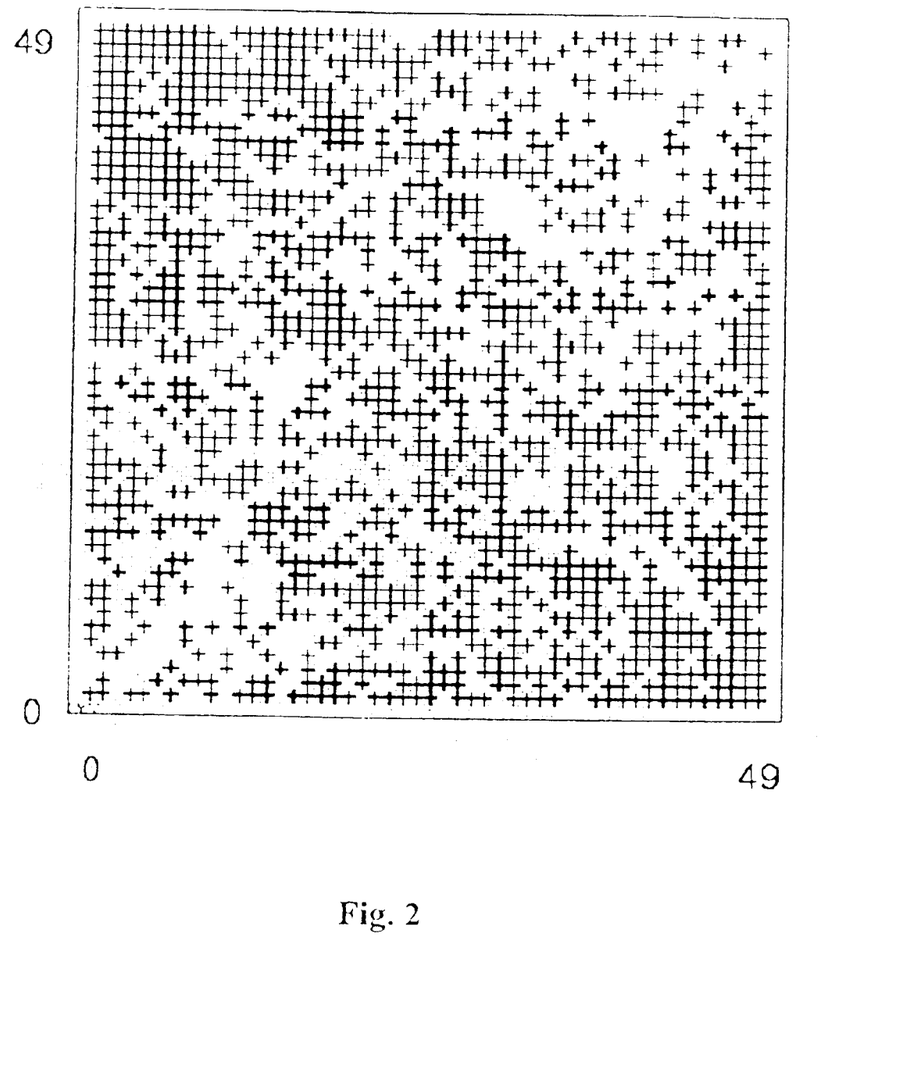
FIG. 2 illustrates the distribution resulting from a molecule sorting step.

The result of the sorting is a molecule distribution over the grid, wherein a grid point can be populated by several molecules, whereas other grid points may remain free. FIG. 2 illustrates the resulting map after three learning phases.

Figure 3:
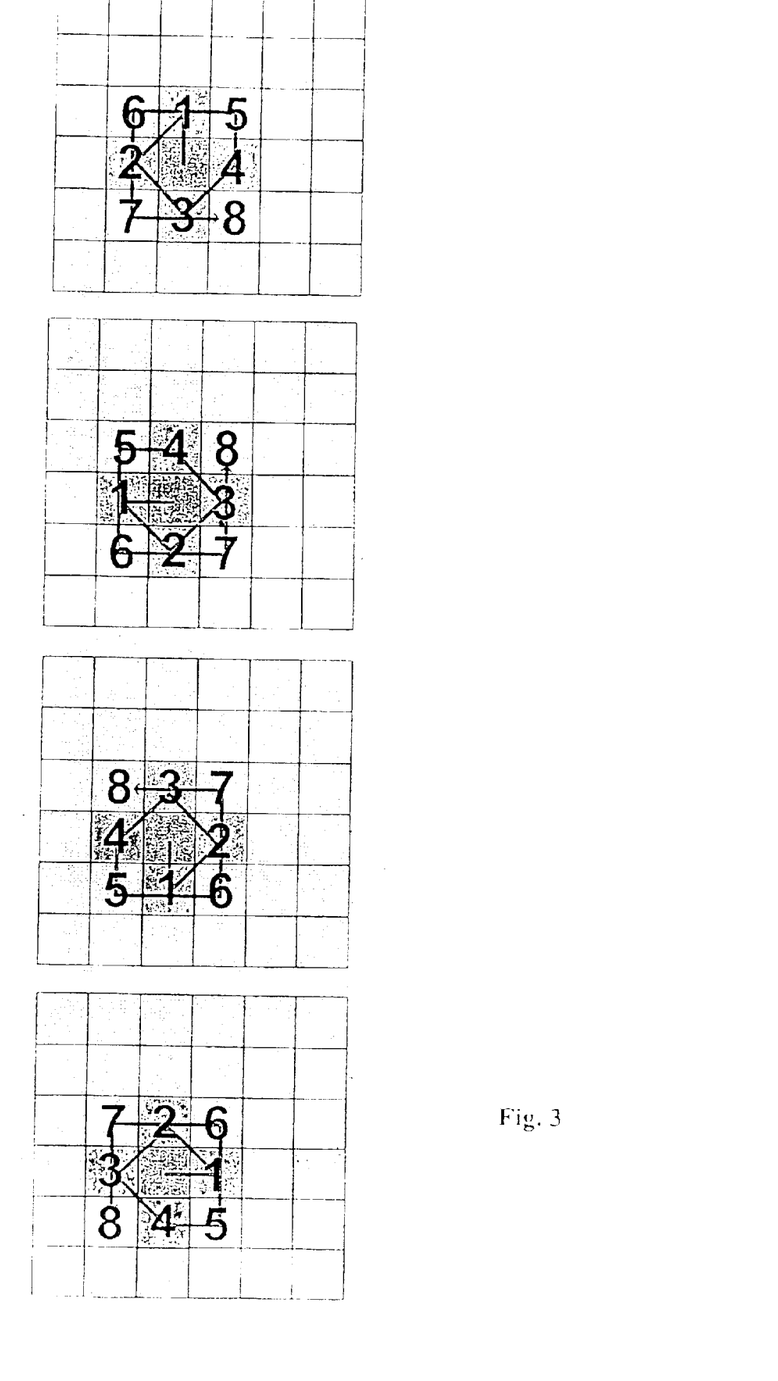
FIG. 3 illustrates the de-clustering step.

Although such an irregular population of the molecule map does actually not hinder the further processing of the molecule map, the molecule map is de-clustered, i.e., molecules which are placed together with others on the same grid point, are placed onto free grid points in their neighbourhood. This is accomplished by a search for a free grid point according to the following scheme (see FIG. 3): The search begins at one of the four direct adjacent grid points (upper, lower, left, right grid point). The first one of these points is randomly selected. The molecule is placed thereon, whether that point is free or not. If that point has been free before the search is successfully terminated. Otherwise, if that point has been occupied before, the search for a free point continues with the next three adjacent grid points. If there is no free point found, the four diagonal neighbours (at the corners) are searched. If there is no free point neither, the respective molecule remains at the place where it has been placed, i.e. the first one of the adjacent grid points. For the point which has been initially at that place, the same search is performed. If after a predetermined number n of iterations there is one molecule left, that molecule is discarded. However, it has been empirically found that already for n=4, there is no molecule to be discarded.

Note that the border of the grid is taken as occupied points. If a border point is reached, the search is continued until the search is back within the grid area.

Figure 4:
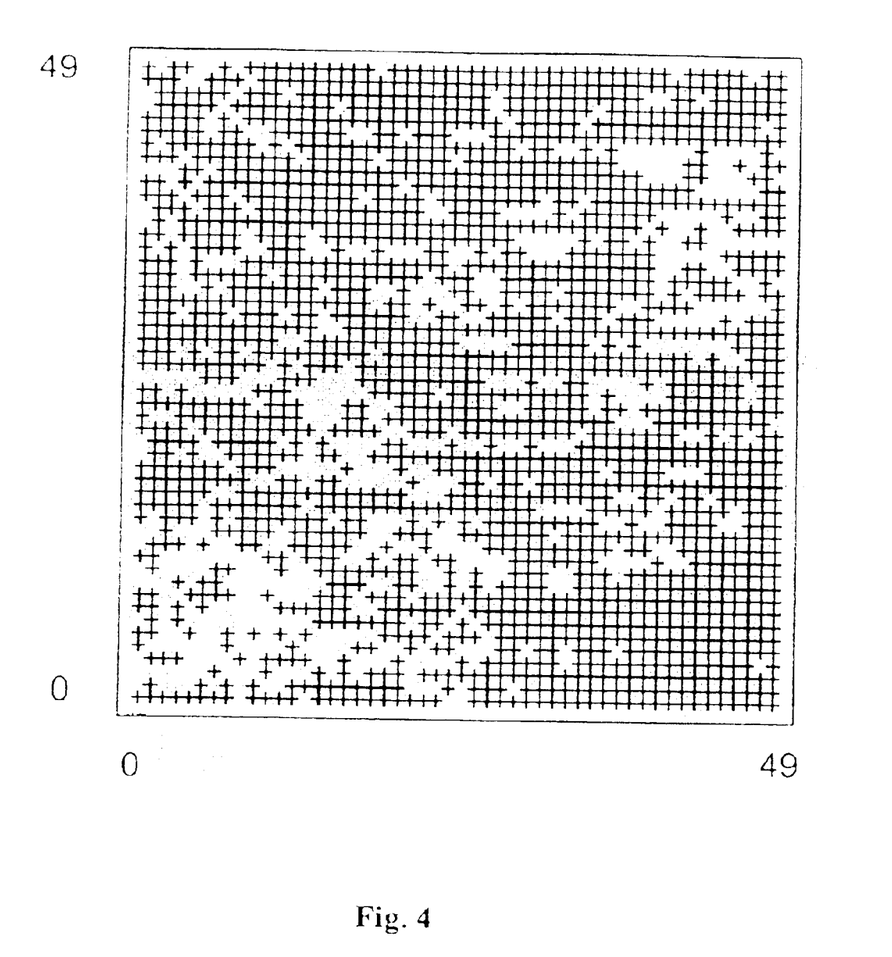
FIG. 4 illustrates the distribution resulting from de-clustering.
Figure 5A:
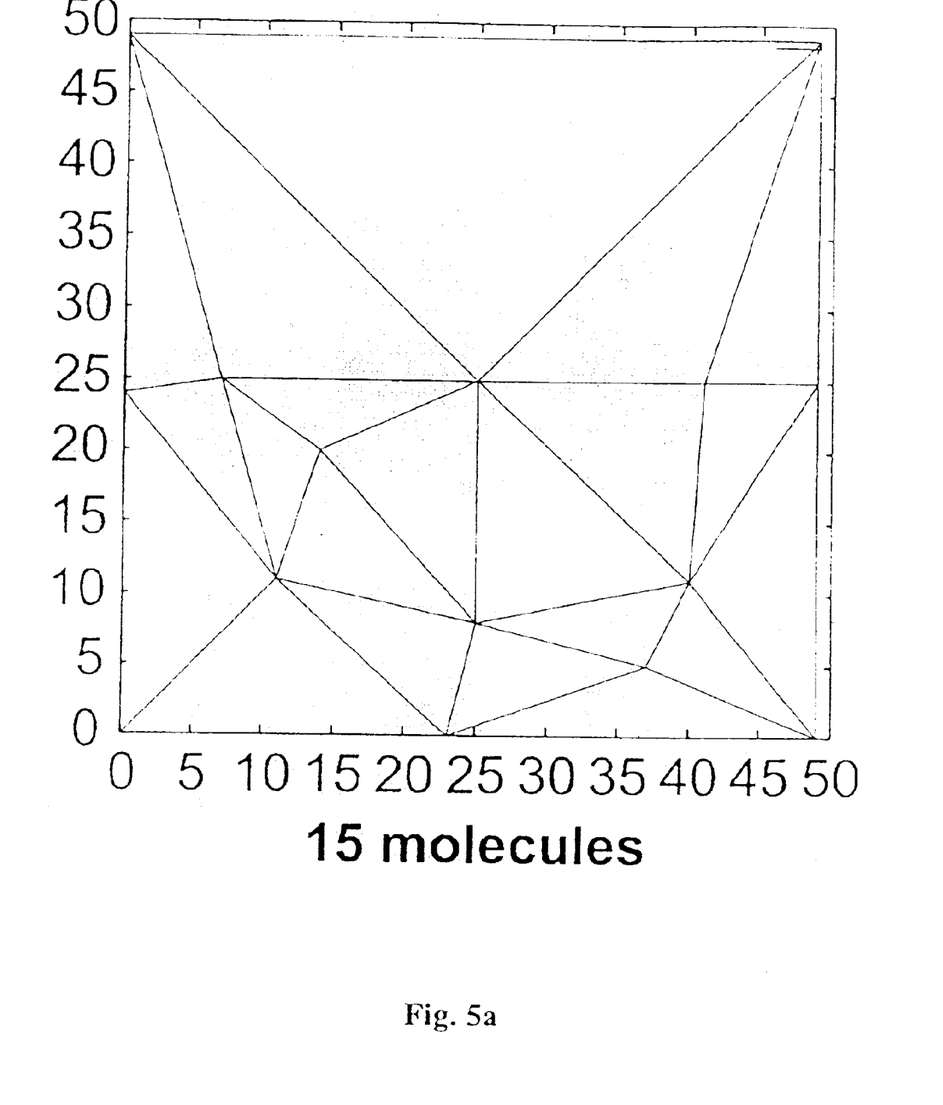
FIG. 5a illustrates the first intermediate step with 15 molecules of approximation of a surface by Delauney triangulation.
Figure 5B:
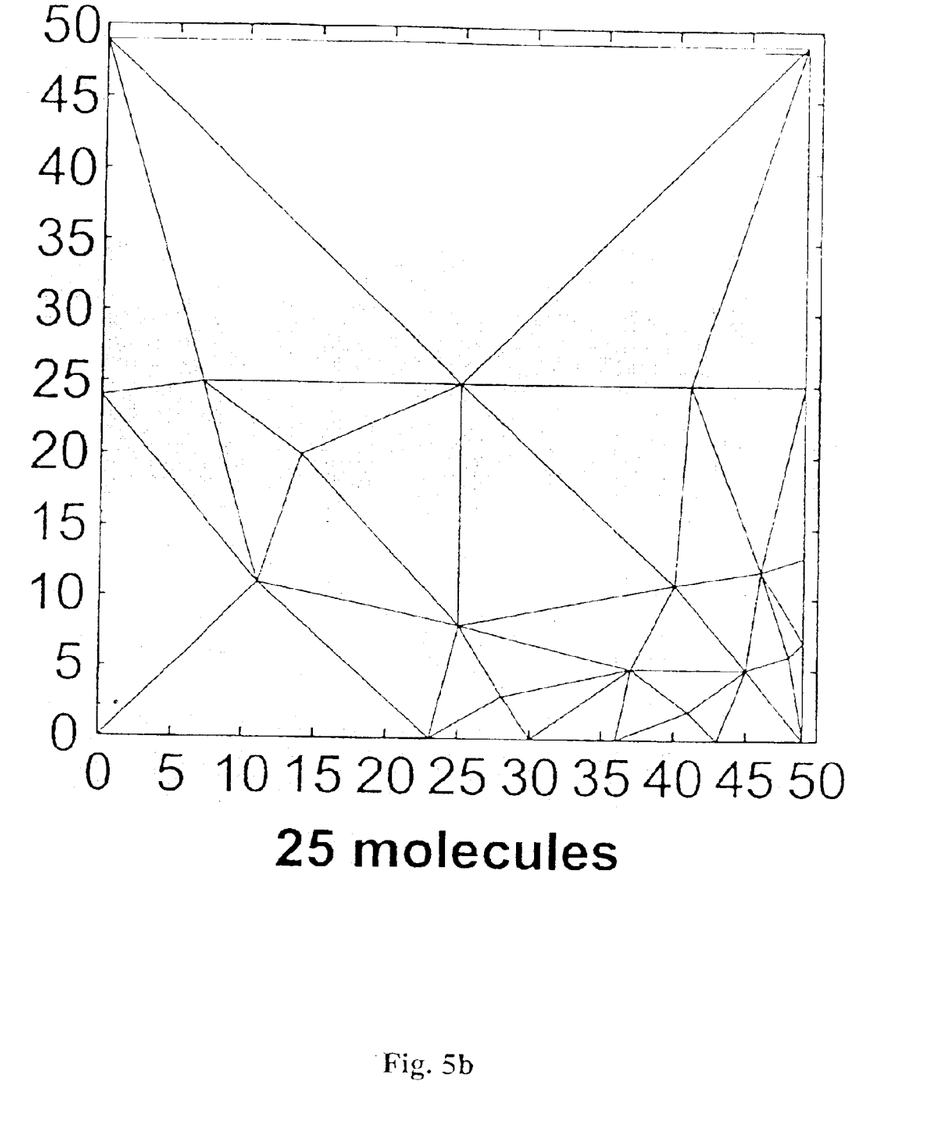
FIG. 5b illustrates the second intermediate step with 25 molecules of approximation of a surface by Delauney triangulation.
Figure 5C:
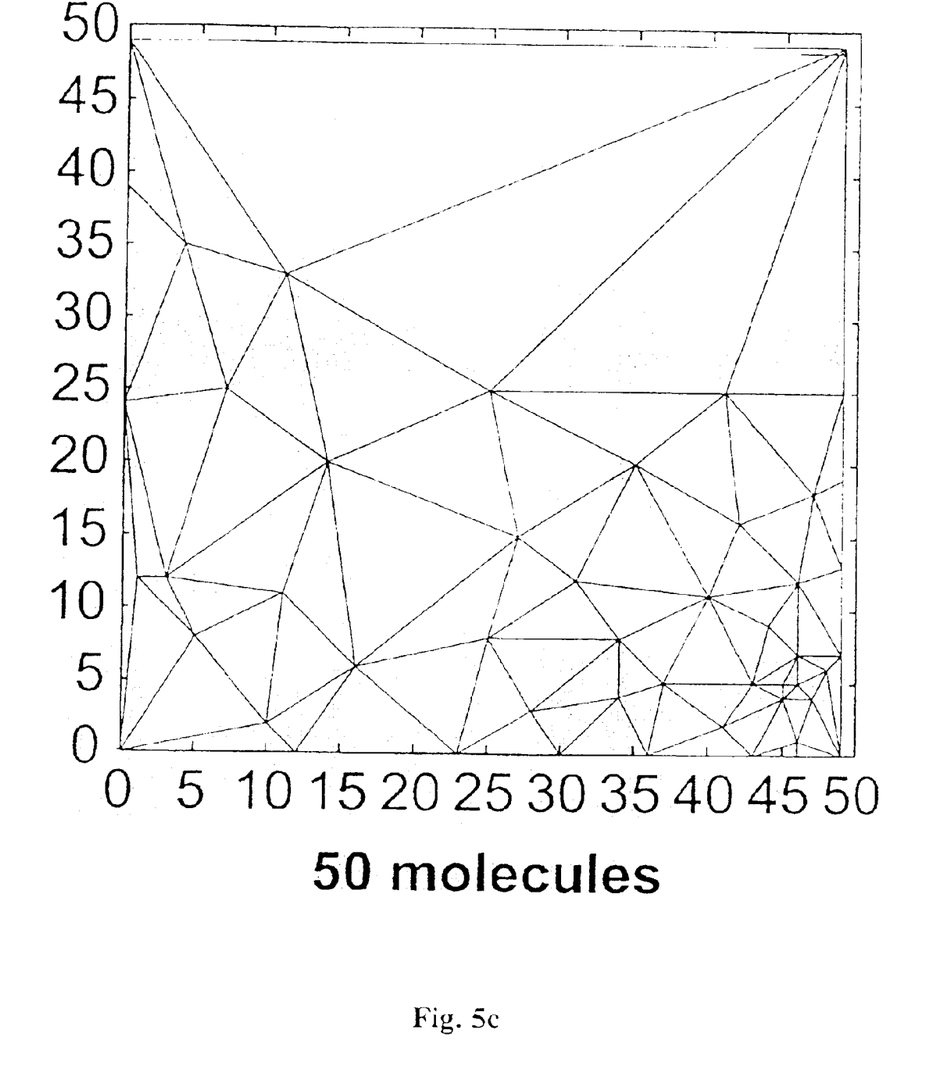
FIG. 5c illustrates the third intermediate step with 50 molecules of approximation of a surface by Delauney triangulation.
Figure 5D:
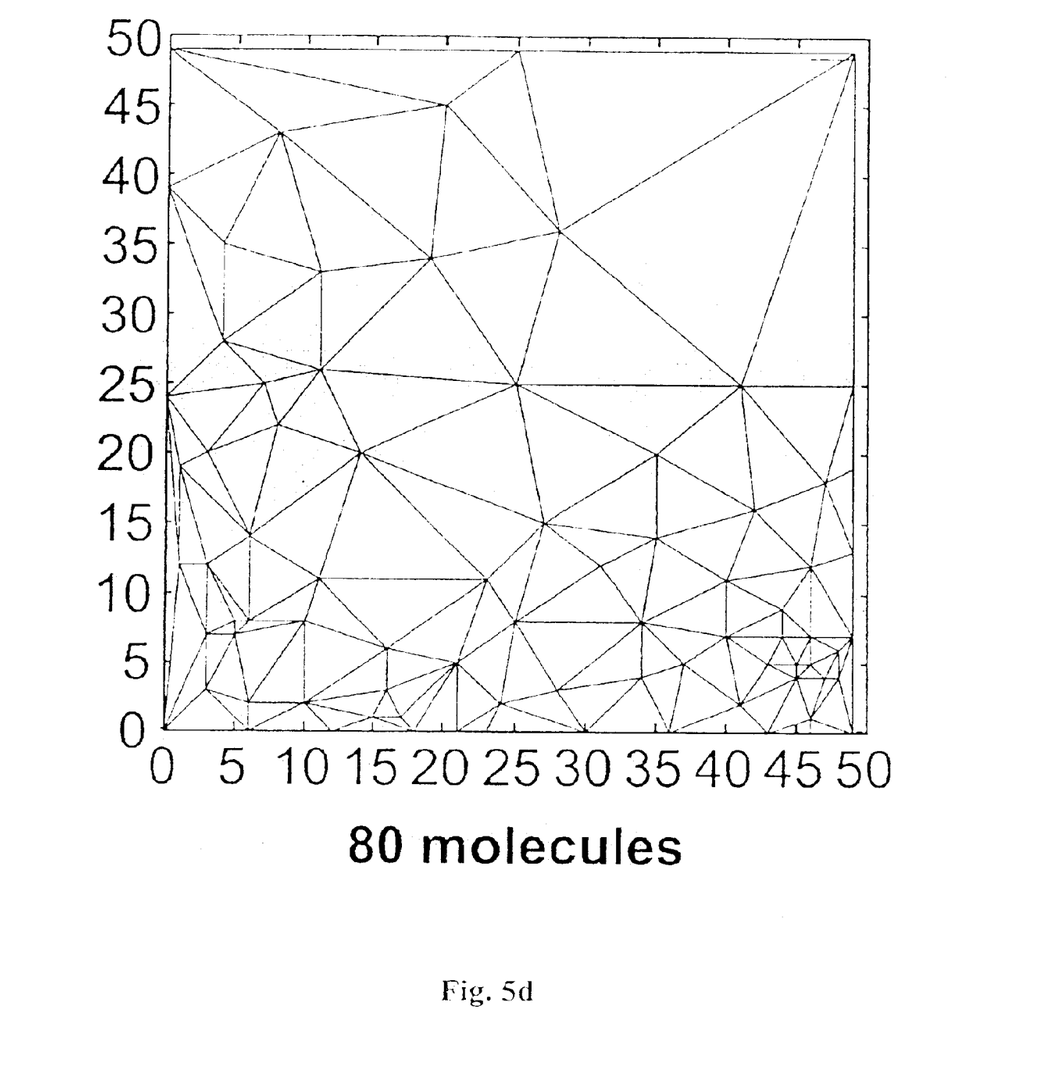
FIG. 5d illustrates the first intermediate step with 80 molecules of approximation of a surface by Delauney triangulation.

The result of this step is a distribution of the molecules over the grid wherein no grid point is occupied by more than one molecule. FIG. 4 shows the resulting distribution. It is to be noted that this de-clustering method conserves the neighbourhood relations between the molecules.

Up to now, the inventive method is not specific for a certain receptor or certain target. The following steps, however, are specific for the receptor or target. Remember that the aim is to find out the candidate molecules with the highest biological activity with respect to the receptor or target. The biological activity of a molecule can be determined by many different approaches, namely calculations, simulations, or experiments.

Since the determination of the biological activity of all the molecules in the grid would be too much time-consuming, a strategy must be applied to reduce the number of possible candidates for further evaluation. Key idea is that adjacent molecules on the grid will have similar values of biological activity due to their similarity in properties (as expressed by the descriptors). However, note that concrete values of the biological activity are not directly known from the descriptors. These values must be determined by using the above-mentioned (very time consuming) methods.

The most straightforward approach to search those molecules having the highest values of biological activity over the molecule distribution would consist in computing all values of the molecule grid. However, such an exhaustive approach would be too much time consuming. Thus, an approximative modelling of the surface has to be performed.

An approximative modelling of the surface by determining activity values of molecules on regularly spaced grid points all over the grid would exhibit the danger of stepping over some interesting minimum/maximum values.

Therefore, an adaptive search is performed in which interesting regions of the grid are evaluated more precisely than other regions of the grid.

The distribution of the biological activity over the molecule grid is modelled as a 3-D surface representing the biological activity of the molecules over the grid. The problem of finding out suitable molecules is transformed into the problem of finding the grid points (i.e., the molecules) having the highest values of biological activity.

As most suitable approach for approximating the biological activity surface, the Delauney Triangulation method has been found. The Delauney Triangulation method consists in approximating a surface by iteratively decomposing it into triangles, whereby the number of iterations is increased at regions of the surface which are more shaped, i.e., regions with great differences in activity values.

Initially, the activity values of the four corner points of the grid are calculated. Based on these four points, the surface is approximated (i.e., decomposed) by two triangles. For each of the resulting triangles, a quality criterion is computed which defines the quality of approximation of the surface by the respective triangle. As quality criterion, the following expression has been found to be suitable:

$$DF(i) = \frac{\sum_{j \in nb_i} \|\nabla_i - \nabla_j\| \cdot \sum_{j \in nb_i} \|f(j)\|}{\#nb_i} \lambda(i) \cdot \kappa$$

The quality criterion $DF(i)$ is proportional to the sum of all gradient values $\nabla_i$, $\nabla_j$ at the corner points i, j and to the average of the functional values $f(j)$ over the number of corner points $\#nb_i$ of the respective triangle i. Further, the quality criterion is inversely proportional to the surface area $\lambda(i)$ of that triangle. The factor $\kappa$ is a scaling factor, which is determined according to the needs for displaying the surface. Thus, using this quality criterion leads to a better decomposition of regions which comprise molecules having great differences in activity. Since the surface area of the triangles is taken into account, large triangles will be treated even if they do not comprise molecules having particular great differences in activity.

As further grid point whose activity is calculated, the center of gravity of the triangle having the worst quality factor (corresponding to the grid region under the surface having the greatest changes in activity) is selected. Based on this calculated point and all precedingly calculated points, a new decomposition of the whole grid surface into triangles is performed. Again, for each of the triangles, the respective quality factor is calculated in order to select a further point of calculation for refining the decomposition.

Figure 6A:
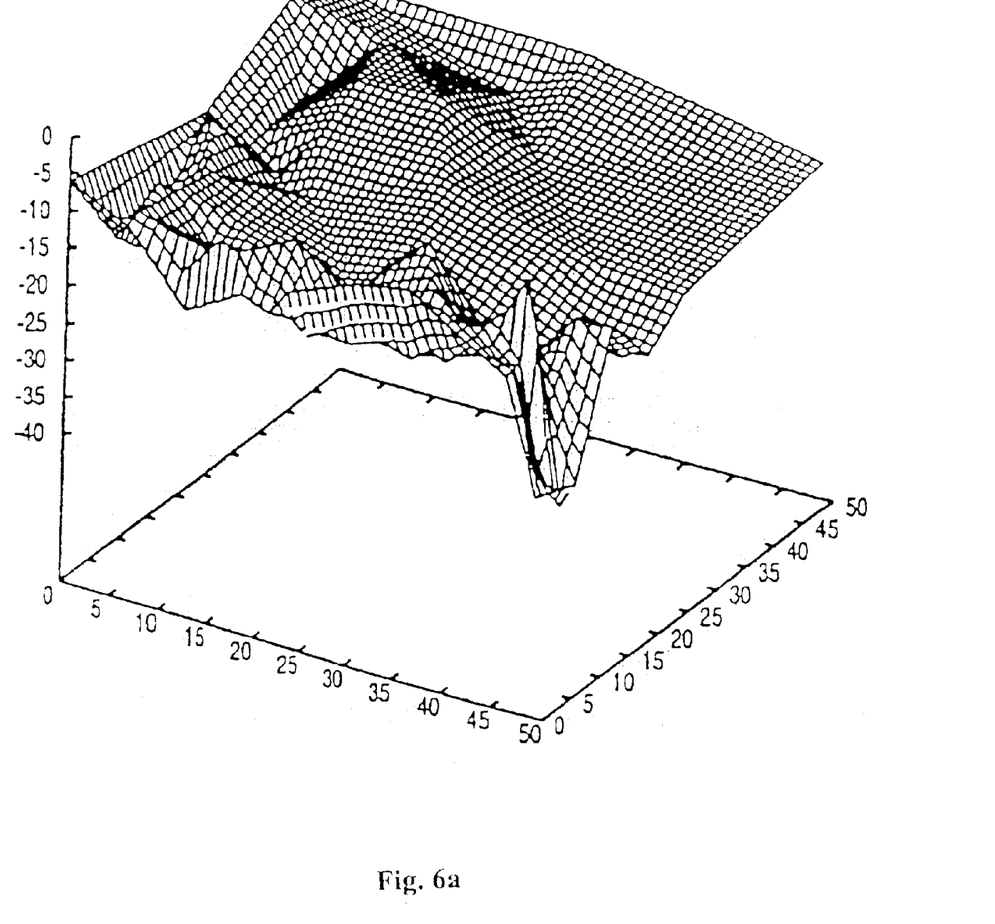
FIG. 6a illustrates the final approximation of the surface of Delauney triangulation.
Figure 6B:
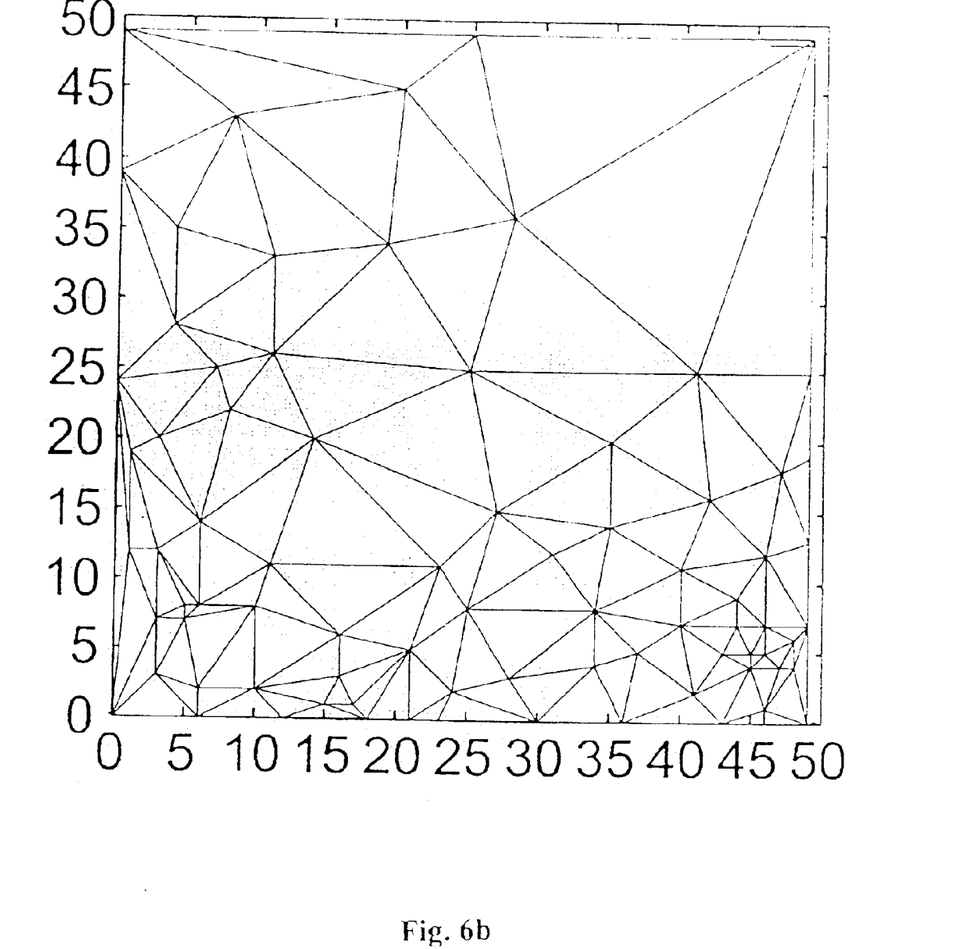
FIG. 6b illustrates the final approximation of the surface by Delauney triangulation.

This step is iteratively performed. FIG. 5 shows the respective decomposition for four iteration steps, namely 15, 25, 50, 80 calculated molecule grid points. The iteration is stopped when the decomposition has become exact enough, i.e., when a predetermined stop criterion is reached, e.g., 5% of all grids points are calculated, or the General error function (sum of all quality factors) reaches a predetermined threshold. The grid surface can then be considered to be optimally approximated with respect to the interesting regions of the grid, i.e., the regions with grid points having the highest values of biological activity, as can be seen in FIG. 6.

Then, in the last step, all the molecules within a predetermined radius around the grid points having the highest biological activity are explicitely evaluated.

All these points are the resulting molecules identified as candidates for further pharmaceutical research.

By applying this method, at least 94% of computing time with respect to an exhaustive evaluation can be saved. Further, due to the pre-sorting step, the optimum candidate molecules are nearly in every case found.

The identified molecules may be tested in suitable biological assays as described for instance by R. Bolger, "High-throughput screening: new frontiers for the 21$^{st}$ century", published in DDT, Vol. 4, No 6, pp. 251–253, June 1999, or by J. S. Major, "Challenges of high throughput screening against cell surface receptors", J. of Receptor and Signal Transduction Research, 15(1–4), pp. 595–607, 1995.

The method according to the invention was evaluated on a data set consisting of 40000 molecules from the World Drug Index (WDI). Some modifications compared to the basic method have been made in order to accelerate the processing.

The molecular descriptor was calculated for all the molecules. The sorting step took place on a rectangular 250×250 neuron SOM (i.e., on 62500 grid points). Instead of putting the molecules in an arbitrary way onto the grid (FIG. 1), the weight vectors of the 62500 neurons of the self organizing map (SOM) were initialized according to the first eigenvectors of the complete molecule descriptor matrix, i.e., the 40000×6 matrix. Therefore, the de-clustering step as described above could be stepped over.

Figure 7:
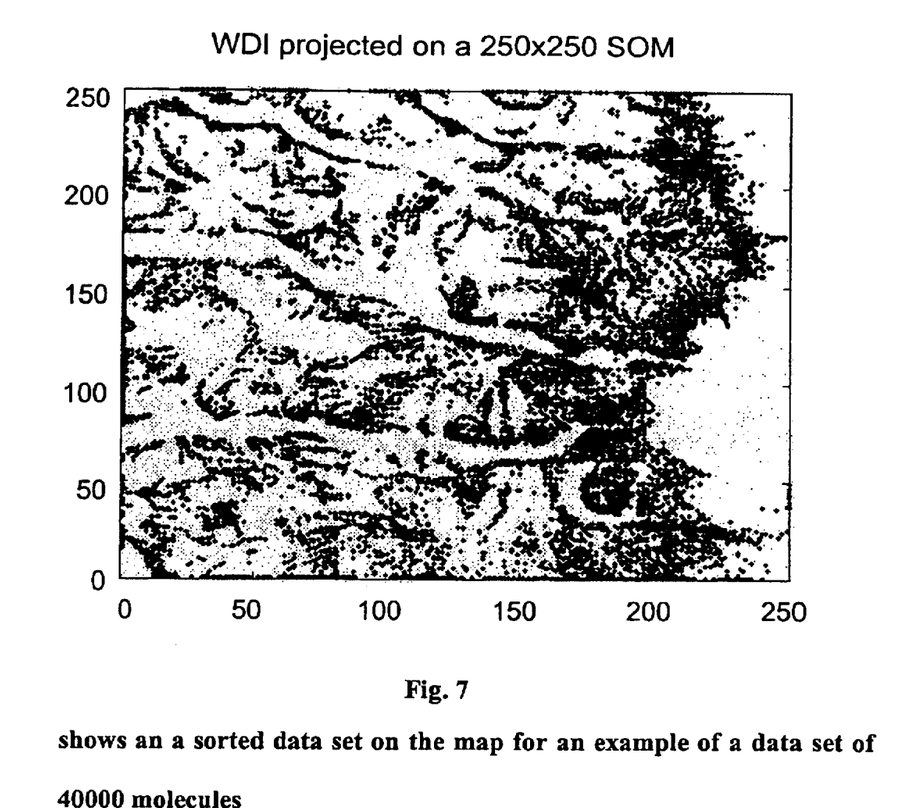
FIG. 7 shows an a sorted data set on the map for an example of a data set of 40000 molecules, FIG. 8 displays the amount of active molecules for a first target according the example of FIG. 7, FIG. 9 displays the amount of active molecules for a second target according the example of FIG. 7, FIGS. 10 and 11 show the percentage of active molecules related to the total amount of active molecules contained in the dataset for the results according to FIGS. 8 and 9, respectively.

Then the training of the SOM was performed with a convergence of 0.2, and an amount of propagation of 15. A Gaussian neighborhood function was used. The learning was performed over 5 phases while the amount of propagation was decreased stepwise to 1 proportional to the elapsed learning time. FIG. 7 shows the sorted data set on the map.

Then, the distribution of the biological activity was modeled. Prior to the triangulation steps, a convex hull around all molecules on the grid was calculated, by using 8 to 12 points of the grid. The resulting points were taken as a part of the initial data points. The other points used are the mean and the means of the four quadrants.

At these points, the biological activity of the underlying molecules was determined, and the initial triangulation was calculated. The docking calculations were performed for both thrombin and dihydrofolatreduktase (DHFR) receptors. For each of the resulting triangles, the quality criterion DF(i) was computed. The number of iterations for the triangulation was 2000.

As a last step, candidate molecules with a binding energy below –30 kJ/mol were selected and the biological activity of all molecules lying in the first and second neighborhood circle around these points was determined. The total amount of found molecules with an activity below –30 kJ/mol was calculated at this point and used as a measure for the performance of the algorithm.

The complete algorithm was applied to both receptors thrombin and DHFR. As explained earlier, the SOM needed to be calculated only once. For both receptors, the calculation was terminated after 2000 iterations, i.e. 5% of molecules were calculated.

The whole procedure including the subsequent refinement took about 4000 minutes for the Docking (ca. 2 minutes per molecule) and 12 hours for the SOM calculation, which had to be performed only once. This means an acceleration of about factor 8 for one investigation and an acceleration of 20 for all further runs for further targets based on the same SOM.

Figure 8:
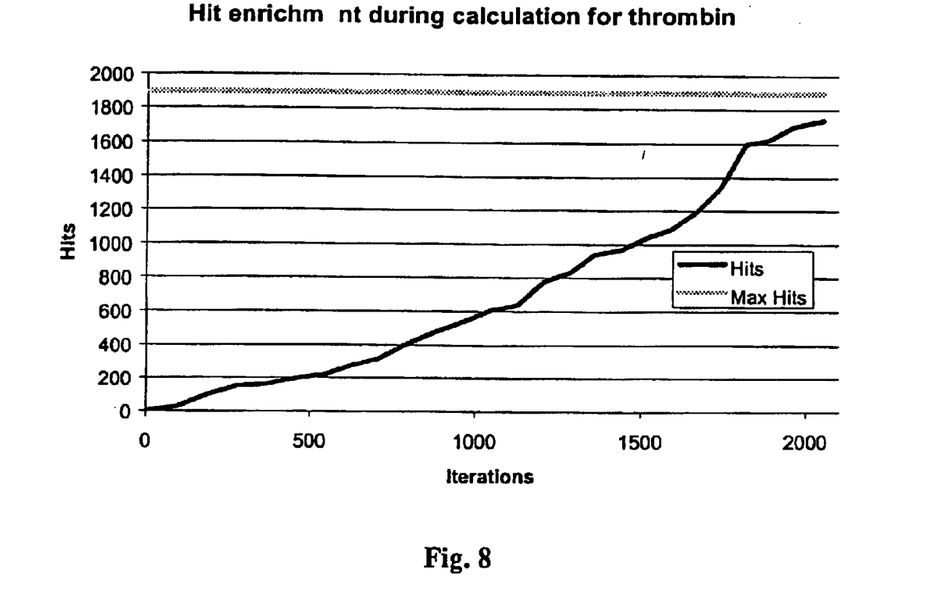

FIG. 8 displays the amount of active molecules (hits) found during the iterations for the thrombin receptor. The algorithm was finished after 2000 iterations. The horizontal gray line shows the total amount of hits present in the WDI for that specific receptor.

Figure 9:
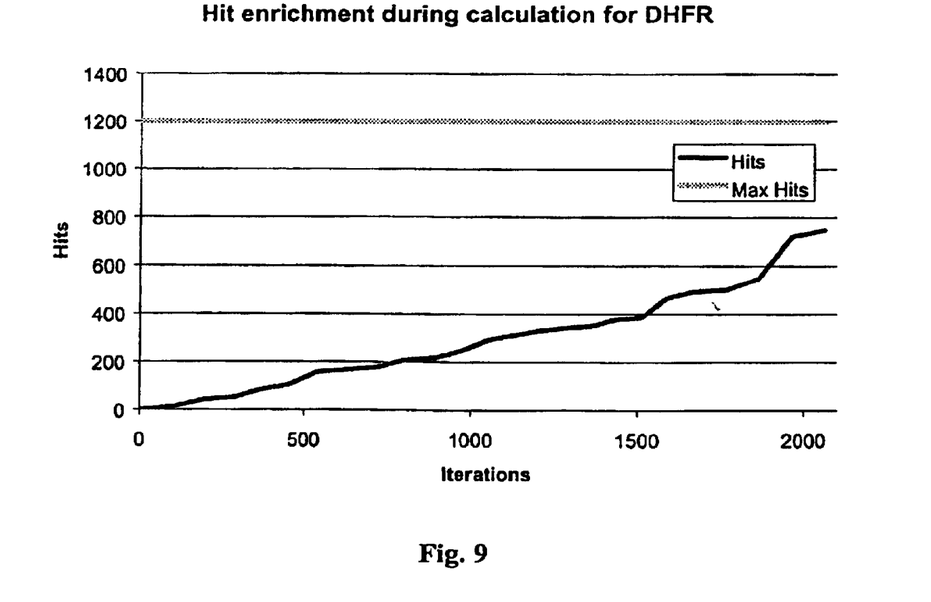

FIG. 9 display the amount of hits during the 2000 iterations for the DHFR receptor. The horizontal gray line shows the total amount of hits present in the WDI for that specific receptor.

Figure 10:
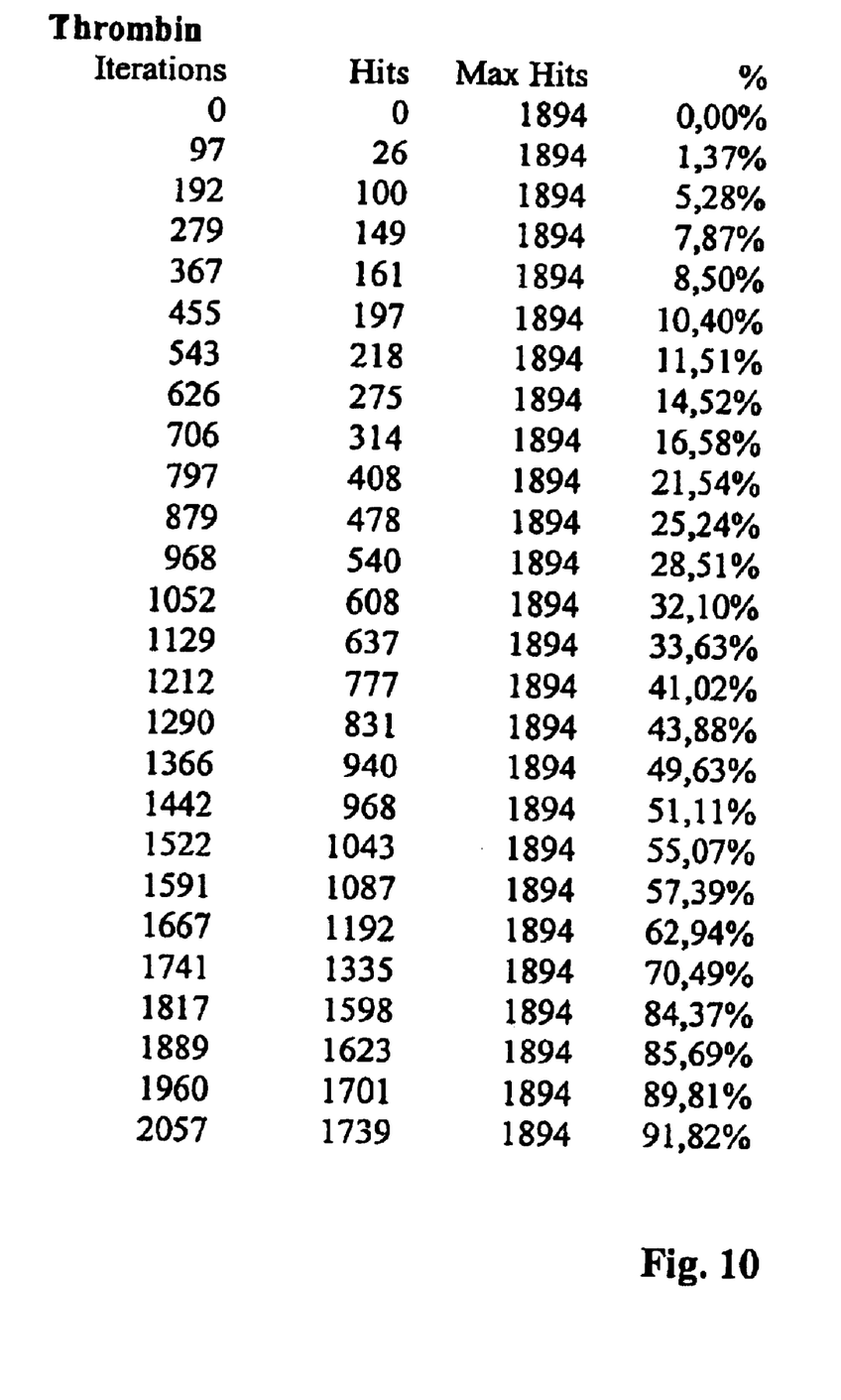
Figure 11:
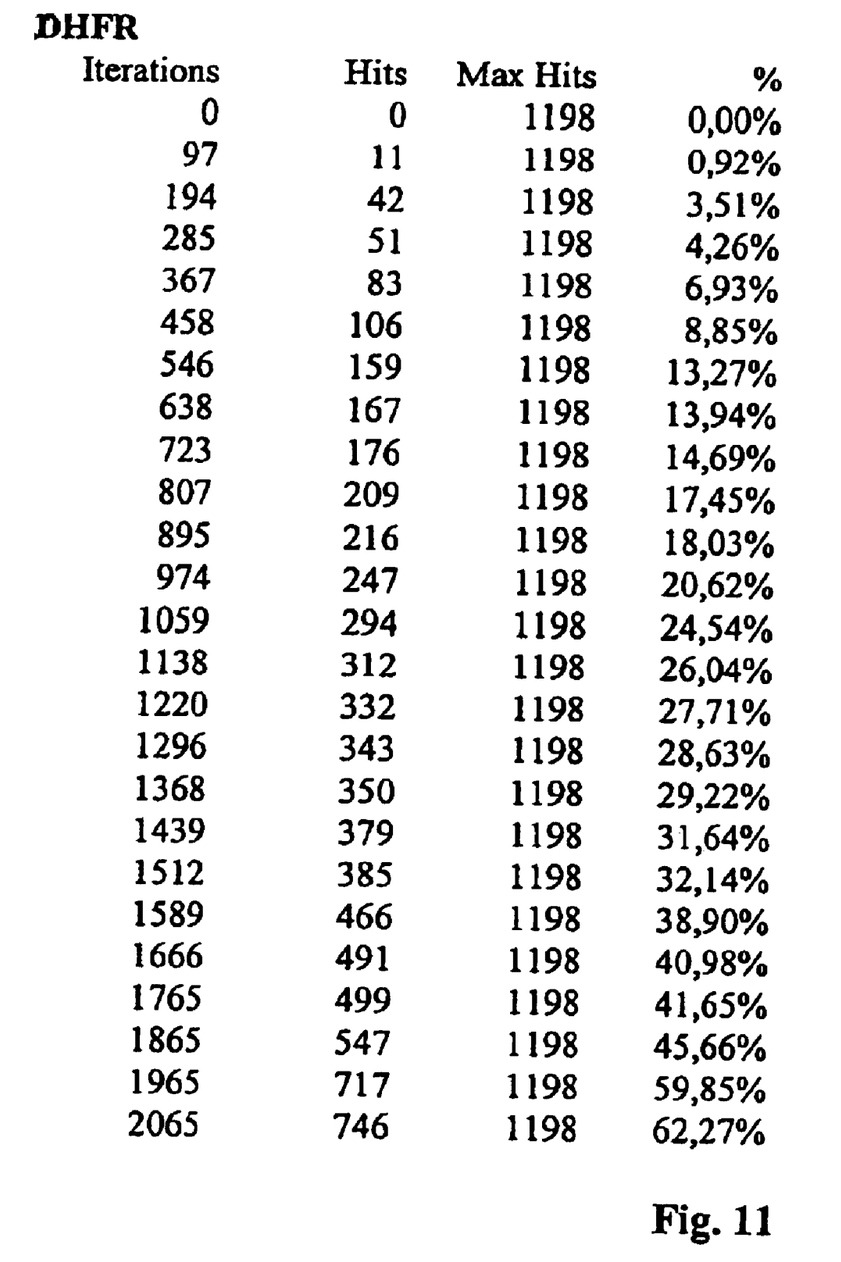

FIGS. 10 and 11 show the percentage of hits related to the total amount of hits as a function of the number of iterations for thrombin, an DHFR (Dihydrofolatreductase), respectively.

What is claimed is:

1. A computer-implemented method of identifying candidate molecules expected to be biologically active, said method comprising the following steps:

a) creating a set consisting of different molecules;

b) to each of said molecules of said set, assigning a descriptor representing a predetermined number of molecular properties;

c) mapping said set of molecules onto points of a two-dimensional grid with regard to a predetermined similarity relation of the respective assigned descriptors such that the grid distance between grid points of two molecules is a measure for the similarity of said two molecule descriptors;

d) forming a three-dimensional surface over said grid of molecules, said surface representing the distribution of biological activity of the molecules on the grid approximatively according to a predetermined quality criterion;

e) selecting from said three-dimensional surface candidate molecules satisfying a predetermined criterion with respect to their biological activity.

2. The method according to claim 1, wherein said three-dimensional surface in step d) is formed by applying the following steps:

da) taking the whole two-dimensional grid as initial region of approximation;

db) selecting molecules on predetermined grid points of said region, and calculating their respective values of biological activity;

dc) approximating the surface over said region using said previously determined values of biological activity of said molecules on said predetermined grid points;

dd) determining whether said approximated surface satisfies a predetermined quality criterion; if so, goto step e); if not so, refining the approximation of the surface by selecting molecules on further grid points, calculating their respective values of biological activity, and repeating step dc) and this step dd).

3. The method according to claim 1, wherein said three-dimensional surface in step d) is formed by an approximation by triangles according to a method of the Delauney Triangulation type.

4. The method according to claim 1, wherein said selected candidate molecules are suitable for chemical synthesis.

5. The method according to claim 1, whereby the molecular properties represented by said descriptors are at least two of:

molecular weight, number of rotatable bonds, number of hydrophobic groups, number of hydrophilic groups, number of acid groups, number of basic groups, number of neutral groups, number of zwitter groups, number of heavy atoms, number of H-bond donors, number of H-bond acceptors, number of 1–2 dipoles, number of 1–3 dipoles, number of 1–4 dipoles.

6. The method according to claim 1, whereby the molecular properties represented by said descriptors are:

molecular weight, number of rotatable bonds, number of hydrophobic groups, number of heavy atoms, number of H-bond donors, number of H-bond acceptors.

7. The method according to claim 1, whereby the molecular properties represented by said descriptors are at least two of:

molecular weight, number of rotatable bonds, number of hydrophobic groups, number of heavy atoms, number of H-bond donors, number of H-bond acceptors.

8. The method according to claim 1, wherein said molecule-mapping is performed using self-organizing maps within a neural network or statistical methods.

9. The method according to claim 1, wherein said similarity relation is defined by a metric measure of the molecular properties represented by said descriptors.

10. The method according to claim 1, wherein between step c) and d) there is a step of re-mapping said molecules on said grid such that no grid point is occupied by more than one molecule, whereby said similarity relation between each two points is conserved.

11. The method according to claim 1, wherein forming said three-dimensional surface is performed using computational or experimental identification of biological activity.

12. The method according to claim 1, wherein said predetermined criterion of biological activity is minimum value of biological activity.

13. The method according to claim 1, wherein said set of molecules is held in a computerized database.

14. The method according to claim 1, wherein said predetermined locations of step db) are corner points of the respective region.

15. The method according to claim 3, wherein the quality criterion is defined by:

$$DF(i) = \frac{\sum_{j \in nb_i} \|\nabla_i - \nabla_j\| \cdot \sum_{j \in nb_i} \|f(j)\|}{\#nb_i} \lambda(i) \cdot \kappa$$

with i: the respective triangle, j: the corner points of triangle i, f(j): the value of biological activity of point j, $\nabla_i, \nabla_j$: value of a gradient operation applied on point i, j, $\lambda(i)$: surface area of triangle i, $\kappa$: a scaling factor, nb: number of corner points.

16. The method according to claim 2, wherein said stop criterion is defined by the sum over all values of the quality criterion calculated in one step.

17. The method according to claim 2, wherein said stop criterion is defined by a predetermined number of calculated grid points.

18. The method according to claim 1, wherein on the grid around each selected molecule in step e), biological activity values of a predetermined number of adjacent molecules are calculated.

19. The method according to claim 1, comprising a step of visualizing the assigned points of said 2-D grid.

20. The method according to claim 1, comprising a step of visualizing the resulting 3-D surfaces.

21. A computer system comprising means for performing the method according to claim 1.

22. The computer system according to claim 21 comprising means for communicating with a database comprising said set of molecules.

23. A data storage means storing a program for performing the method according to claim 1.

24. A program for storing a database comprising the set of molecules for use with the method according to claim 1.

25. A Method of producing molecules determined by the method according to claim 1.

26. The method according to claim 25, further comprising step f) of testing said found candidate molecules in a suitable biological assay.

27. The method according to claim 8 wherein the statistical methods include linear vector quantization.

* * * * *